United States Patent [19]
Eilender

[11] Patent Number: 5,019,064
[45] Date of Patent: May 28, 1991

[54] LOW FRICTION MULTILAYER PAD WITH FOAM BACKING

[76] Inventor: Kasriel Eilender, 305 E. 86th St., New York, N.Y. 10028

[21] Appl. No.: 530,189

[22] Filed: May 29, 1990

Related U.S. Application Data

[63] Continuation-in-part of Ser. No. 297,977, Jan. 17, 1989, Pat. No. 4,959,059.

[51] Int. Cl.<sup>5</sup> ............. A61F 13/00; A61F 13/15
[52] U.S. Cl. ........................... 604/378; 604/381; 128/889; 128/619; 428/160
[58] Field of Search ................ 604/381, 378; 128/112.1, 619, 622, 588, 889; 428/423.1, 423.5, 423.7, 160, 131

[56] References Cited

U.S. PATENT DOCUMENTS

| | | | |
|---|---|---|---|
| 2,626,889 | 1/1953 | Scholl | 128/112.1 |
| 2,917,847 | 12/1959 | Scholl | 128/622 |
| 3,186,006 | 6/1965 | Miller | 128/622 |
| 3,670,731 | 6/1972 | Harmon | 604/364 |

Primary Examiner—Stephen C. Pellegrino
Assistant Examiner—Gary Jackson
Attorney, Agent, or Firm—Jacob B. Burke

[57] ABSTRACT

This multilayer low friction pad for reducing shear and friction forces on a person's body, and for preventing and treating sores on a person's body caused by shear forces, friction, pressure, chafing and moisture, has a first layer made of soft, flexible foam material which is thick enough to serve as a shock absorber, facilitate handling, and prevent wrinkling and crumpling of the pad. A second layer bonded to the foam layer has a very slippery surface on which is a third layer composed of a slippery lubricant cooperating with the second layer to reduce shear forces and provide a working surface having a negligibly small coefficient of friction. The first layer has an exposed side rough enough to prevent frictionally displacement of the pad while in use. A nonporous fourth layer can be bonded between the first and second layers to serve as a moisture barrier. One or more drain holes can be provided in the pad underlaid by a highly absorbent mat attached to the exposed side of the first layer. The pad can be shaped as a cap, sock, glove, etc. to fit on a body part to be protected from shear forces, friction, pressure, chafing and moisture.

19 Claims, 2 Drawing Sheets

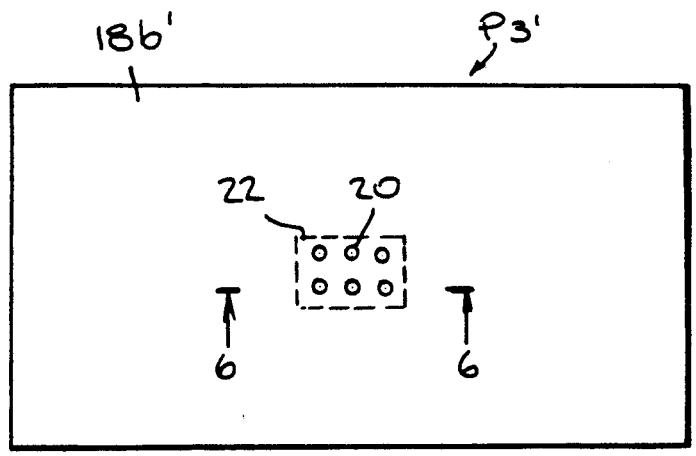
Fig. 5.
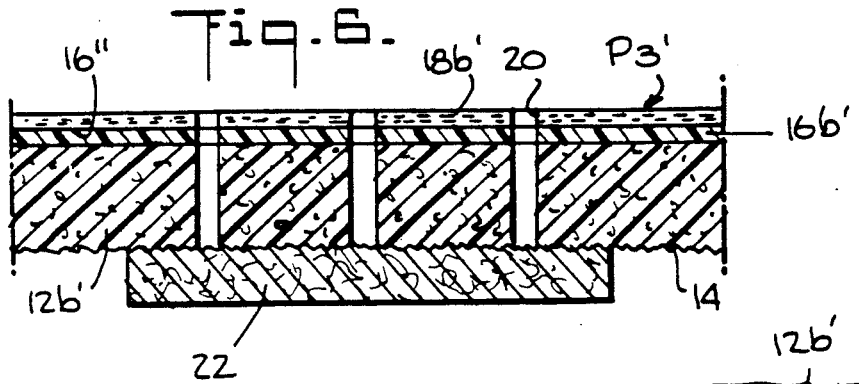
Fig. 6.
Fig. 7.
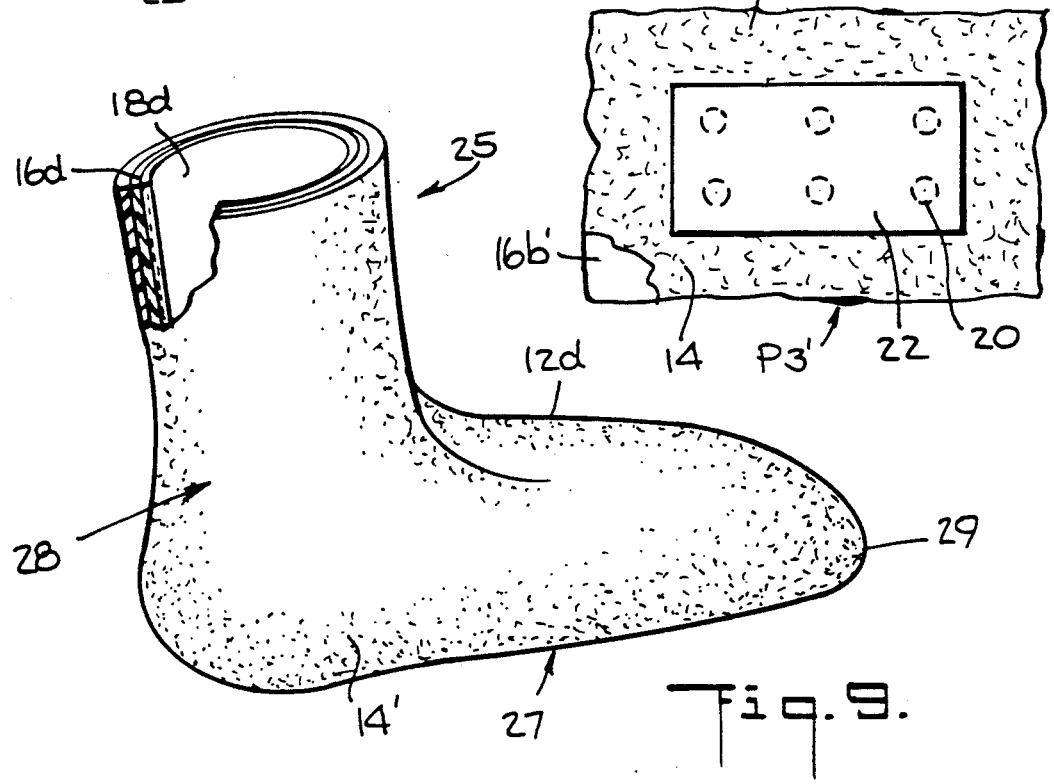
Fig. 9.

LOW FRICTION MULTILAYER PAD WITH FOAM BACKING

This application is a continuation-in-part of copending U.S. Pat. application entitled: "Improved Low Friction Multilayer Pad", Ser. No. 297,977, filed Jan. 17, 1989, now U.S. Pat. No. 4,959,059, dated Sept. 25, 1990.

BACKGROUND OF THE INVENTION

1. Field of the Invention

This invention concerns improved low friction multilayer pads for reducing and preventing bedsores, decubitus ulcers, and similar lesions caused by shear forces, friction, pressure, and moisture. Besides acting as shear and friction reducing modalities, the pads can help to manage or contain fecal excretions and urine of incontinent individuals, and other body discharges of persons who are bedridden or confined to wheelchairs. The pads are not limited to use by ill persons. They can be used in ambulatory settings by athletes and others. For such usages the pads can be shaped to fit any particular body parts which are subject to shear forces, friction, chafing, abrasions, undue pressure, and moisture to prevent or alleviate adverse effects caused by such conditions upon affected body parts.

2. Description of the Prior Art

In copending parent patent application Ser. No. 297,977filed Jan. 17, 1989, now U.S. Pat. No. 4,959,059 above mentioned, there is disclosed a multilayer pad having two upper lubrication layers. These layers are applied to a porous intermediate layer superimposed on a nonporous backing layer. The porous and nonporous layers are joined by a peripheral seam so that they can slip and slide in part with respect to each other. The exposed side of the nonporous layer is smooth and slippery. This structure is inexpensive to manufacture and can be discarded after a single use. It has however some limitations in use due to its overall thinness, the peripheral attachment of the porous and nonporous layers, and the slippery bottom surface of the pad.

BRIEF DESCRIPTION OF THE INVENTION

In the following description of the invention, the terms "foam" and "foamy" layers refer to soft, flexible, lightweight sheets made of plastic, rubber, cellulose or other natural or synthetic materials which have a cellular structure. The cells may be open so that the materials are porous, or they may be closed so that the materials are nonporous. The materials may thus be moisture absorbent or nonabsorbent. Coming within the scope of this definition are porous and nonporous sheets or layers made of felt, i.e. soft, flexible, lightweight masses of compacted fibers. The fibers may be composed of organic or inorganic natural or synthetic substances.

The present invention is directed at overcoming difficulties experienced with prior multilayer low friction pads, and at providing improved low friction pads which can perform functions prior pads could not. The new multilayer pads described herein, each has a bottom or backing layer formed of flexible, relatively thick, spongy foam, foamy, or felt material, provided with an outer exposed rough, nonslippery, friction inducing surface. The foamy backing layer may be porous and moisture absorbent, or it may be nonporous and nonabsorbent to serve as a moisture barrier. On the foamy layer is bonded a porous or nonporous, flexible intermediate layer having a smooth, slippery, low friction inducing top surface. On the intermediate layer is a top laye slippery lubricant. If the intermediate layer and the foamy backing layer are both porous, it may be desirable in some applications to interpose between them a thin, nonporous, plastic film or layer to serve as a moisture barrier. In some applications where the multilayer low friction pad is to be used on a flat surface such as a bed, chairs longue, stretcher, gurney, and the like, one or more drain holes can be provided in the pad underlaid by a highly absorbent mat to take any liquid collected on the pad and draining through the drain hole or holes. The multilayer pad can be preshaped in various ways to conform to the shape of a user's foot, heel, leg, wrist, elbow, knee, back buttock, arm, shoulder, head or other body part. If the intermediate and backing layers are both porous they may take up some moisture, but if excess liquid is generated, the drain hole or holes will serve to drain off the excess liquid into the highly absorbent mat.

The present new pads have the following desirable qualities among others:

1. The thick foam backing layer stabilizes the pad, and inhibits wrinkling and crumpling prior and during use.

2. The pads with or without drain holes, can be used on a bed, stretcher, chaise longue, chair, gurney, table top, or other supporting surface where a person is at risk for developing bedsores.

3. The pads help to contain excrement, urine and other discharges, and to prevent their spreading and spilling out beyond the edges of the pads to the underlying bed sheets, so that the bed sheets do not have to be changed, which results in great savings in time, labor, supplies and bed management.

4. The pads serve as shock absorbing "mini-mattresses" for the user's body as a whole and for affected body parts to which the pads are applied, to help alleviate pressures which are contributory factors in creating bedsores and similar lesions.

5. The rough bottom surface of the pad frictionally grips a bed sheet or other supporting surface so that the pad does not slide around during use.

6. The rough bottom surface of the pad makes it unnecessary to attach the pad to a sheet by supplementary straps or tapes as has heretofore been required.

7. The foam backing layer can be moisture absorbent, so that it will absorb moisture passing through the porous upper layer.

8. If the upper layer is nonporous and the foam backing is porous, the backing layer will absorb moisture when the pad is rolled up to be discarded.

9. The foam backing layer strengthens the structure of the pad, and facilitates handling, use and discarding after use.

10. The foam backing si bulky and provides body to the pad which makes it easier to put in place, and to stay in place during use.

11. The several backing and upper layers are all bonded together throughout so individual parts do not slip and slide with respect to each other during use.

12. Drain holes can be provided in the pad where large amounts of liquid collect, with a highly absorbent mat secured in place under the holes to retain liquids drained through the holes.

13. In all embodiments, the multilayer low friction pad has a layer composed of a slippery lubricant which cooperates with a smooth, flexible, low friction inducing underlying layer in a synergistic way to provide a working surface which reduces the coefficient of friction of the top surface of the pad and also reduces shear forces to negligibly small magnitudes.

14. The softness and flexibility of the pad allow the pad to conform to irregular and nonflat surfaces during use, and to conform to changing positions of the user.

15. The pad is adapted for manufacture into socks, leggings, gloves, caps, wristbands armbands, and other protective garments and covers for various body parts.

16. The pad can easily be cut so that cut pieces can be used in different applications.

BRIEF DESCRIPTIONS OF THE DRAWINGS

FIG. 6 is a greatly magnified cross sectional view taken on line 6—6 of FIG. 5.

FIG. 7 is a bottom plan view taken on line 7—7 of FIG. 6.

FIG. 8 is a greatly magnified fragmentary cross sectional view similar to FIG. 6 of a fifth multilayer low friction pad embodying another modification.

FIG. 9 is an oblique side view on a reduced scale of a sock shaped to receive a person's foot, and made from a multilayer low friction pad.

DESCRIPTION OF THE PREFERRED EMBODIMENTS

Figure 1:
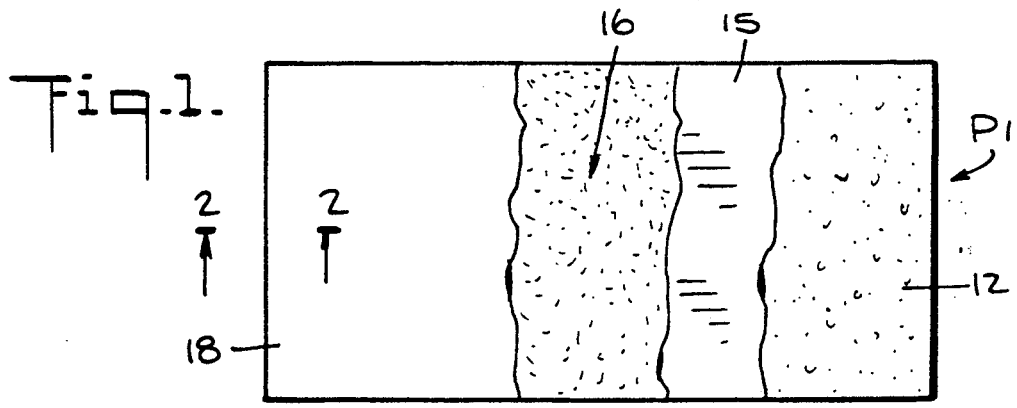
FIG. 1 is a top plan view on a reduced scale of a first multilayer low friction pad embodying the invention, portions of upper layers being broken away to show lower layers.
Figure 2:
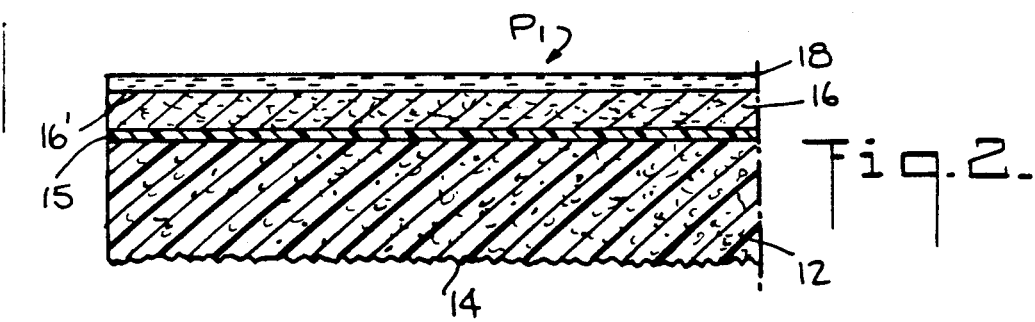
FIG. 2 is a greatly magnified fragmentary cross sectional view taken on line 2—2 of FIG. 1.

Referring first to FIGS. 1 and 2, there is shown rectangular low friction pad P1 having a relatively thick, flexible, soft foam backing or base layer 12 of spongy, porous or nonporous material such as polyurethane or other suitable material which is physically and chemically stable. The layer 12 may have any desired length and width, for example as small as 1 by 6 inches or as large as 36 by 60 inches or more. The thickness of layer 12 is generally uniform and many range from 1/32 of an inch up to about ⅜ of an inch depending on the particular application of the pad. The bottom or exposed side 14 is rough and constructed with projections and irregularities to grip frictionally a surface which it contacts such as a bed sheet during use. Foam layer 12 is thick enough to act as a shock absorber depending on the application in which it is used, to prevent wrinkling of the pad, to facilitate handling without crumpling or collapsing of the pad, and to reduce pressure upon the parts of the user's body in contact with the pad. Superimposed on and bonded throughout to the top surface of layer 12 is a thin nonporous layer 15. The layer 15 serves as a barrier to liquids which may be deposited on the pad during use. Layer 15 prevents liquids from passing into layer 12 if this layer is composed of open cell porous material. Layer 15 also prevents the pad P1 from tearing. Layer 15 can be made of any suitable material such as polyester or polytetrafluorethylene and the like.

Superimposed on and bonded throughout to the layer 15 is a thin layer or sheet 16 whose top surface 16' must be very smooth and have a low coefficient of friction. This layer may be nonporous, porous or perforated. Layer 16 can be made of woven, nonwoven or compacted material, such as rayon, nylon, polyester, or the like. It can be fibrous or solid. The principal quality must be that it presents a low friction surface 16' which is compatible with and coacts with upper layer 18. Layers 12, 15 and 16 can be bonded together throughout by any known process depending on the natures of the materials used; for examples, they can be bonded or fused together thermally, chemically, electronically, etc. with or without adhesives.

On the smooth slippery top surface 16' of layer 16 is applied a generous layer 18 of a slippery lubricant. A suitable lubricant for this purpose may be a surgical gel such as manufacture by Johnson and Johnson under the trademark "K-Y". This and other lubricants can be used without or with added ointments and emollients. Regardless of the formulation of the lubricant, it is essential for the purpose of this invention that it have optimum lubrication properties and that it be compatible with layer 16 to coact with it. The lubricant will penetrate the pores of layer 16 if it is porous. Layers 16 and 18 coact and cooperate with each other to provided a very slippery working surface which has an extremely low coefficient of friction, to reduce to a very low level the shear and friction forces generated during movements of a user's body while it is on the pad. This one of the most important functions of this new low friction pad because shear forces and friction forces are two of the principal causes of bedsores.

In use pad P1 may be placed on a bed sheet covering a mattress, table top, gurney, chair, chaise longue, stretcher or other support. The rough surface 14 of foam layer 12 will frictionally grip the bed sheet and prevent the pad from slipping, sliding, twisting, turning, or other displacement during use. The foam layer 12 also serves as a shock absorber to cushion tissues of the user who sits or lies on the pad. Layer 12 gives body to the pad and makes it easy to handle. Foam layer 12 will also prevent the pad from wrinkling, creasing, crumpling and collapsing during use. While the user is lying on the pad shear and friction forces which tend to cause skin abrasion, bedsores, decubitus ulcers and the like are reduced are to the antifriction properties of the pad. The pad will tend to keep execrement, urine and other discharges from spreading and spilling beyond the edges of the pad. When the pad becomes soiled by perspiration, urine, fecal matter, or other body exudate, or by medicaments, the pad P1 can be removed from the bed or other support, and discarded, while leaving the underlying bed sheet clean and unsoiled. The used pad can be rolled up which will bring the bottom of porous layer 12 into contact with the wet, soiled layers 16 and 18. If layer 12 is sufficiently absorbent, it will absorb free liquids from layers 16 and 18 so that the rolled up pad constitutes a dry unit which can be disposed of in a sanitary manner without mess. Low friction pad pad P1 is intended for one-time usage, so that it will be discarded after a single use. The pad can be made by mass production methods at low cost. It is easy to use and requires no straps or tapes to hold it in place on a bed or chair. It can be used by unskilled personnel without supervision. It can be made of biodegradable materials to present minimum problems in disposition after use.

Figure 3:
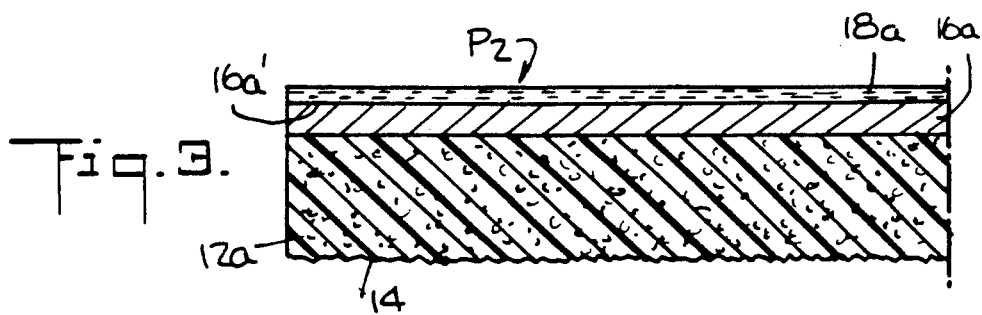
FIG. 3 and FIG. 4 are fragmentary cross sectional views similar to FIG. 2 of second and third multilayer low friction pads respectively embodying modifications of the invention.

In FIG. 3 is shown a second low friction pad P2 which employs a thick bottom, backing or outer layer 12a like layer 12 in pad P1. Foam layer 12a has the rough, frictional exposed bottom surface 14 as in pad P1. Layer 12a can be made like layer 12 of porous or nonporous foam material which is a good shock absorber and gives body to the pad as in pad P1. The nonporous layer 15 of pad P1 is omitted. The foam material of layer 12a serves as a barrier to liquids spilled or exuded on the pad P2. The structure of the foam layer strengthens the pad and functions as in pad P1 to prevent wrinkling and crumpling. Layer 12a cover by woven, nonwoven, compacted or perforated layer 16a which has a very slippery top surface 16a'. Layer 16a is coated with slippery lubricant layer 18a as in pad P1. Layers 16a and 18a coact and cooperate to reduce the coefficient of friction of the top of the pad to a very low magnitude, and to reduce the shear and friction forces which cause bedsores, to negligibly low magnitudes so development of bedsores is prevented. Pad P2 is less expensive to manufacture than the four-layer pad P1 because pad P2 has one less layer; nevertheless pad P2 has proven to be equally effective as an antifriction, antishear modality.

Figure 4:
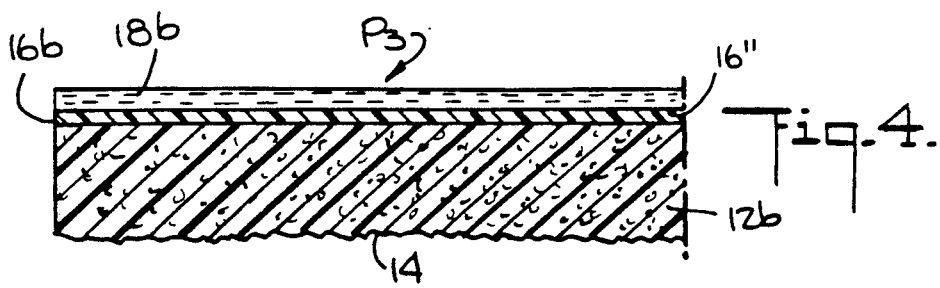

In FIG. 4, low friction pad P3 has thick bottom or backing layer 12b like layers 12, 12a. Layer 12b may be porous or nonporous foam material, with rough, exposed frictional surface 14. On layer 12b is bonded throughout a thin, smooth, nonporous layer 16b which has a very slippery upper surface 16". Layer 16b can be made of a low friction inducing material such a polytetrafluorethylene, nylon, for the like. Lubricant layer 18b like layers 18 and 18a is liberally applied to the upper surface 16" of layer 16. Layers 16b and 18b coact and cooperate in reducing the coefficient of friction of top layer 18b and in reducing shear and friction forces like layers 18 and 18a. Pads P2 and P3 can be used in the same ways as described for pad P1 above. In addition the pads P1, P2 and P3 can be cut in small sizes or strips and applied to any part of the body of a person requiring low friction cover or protection while standing, sitting, lying down, or moving about. Pads P1, P2 and P3 can be used as a joint, arm, wrist, shoulder, leg or back cover or as a protection for any part of the body for which it is desired to reduce or prevent shear, pressure and friction causing sores. Even athletes engaged in running and other vigorous sports will find useful antifriction applications for the pads.

Figure 5:
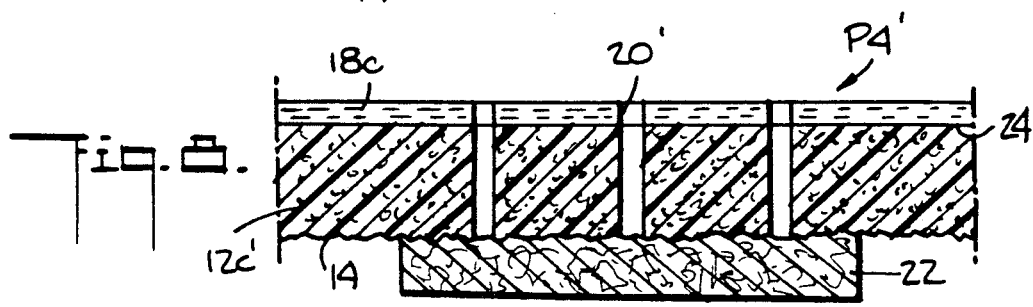
FIG. 5 is a top plan view on a reduced scale of a fourth multilayer low friction pad embodying a further modification of the invention.

There are some applications where a quantity of liquid such as urine, wash water, etc. is discharged upon the multilayer pad while in use. Normally this liquid will be contained by the pad. However the quantity of liquid may be too large for any layer or layers of the pad to absorb. To cope with this situation there is provided low friction pad P3' shown in FIGS. 5, 6 and 7. This pad is similar or identical to pad P3 in construction, with bottom foam layer 12b' having rough frictional bottom surface 14. Nonporous layer 16b' and lubricant layer 18b' are identical to layers 16b and 18b respectively of pad P3. At the center of the pad or whereever liquid collects while the user lies on the pad, there is provided one or more closely spaced drain holes 20. The drain holes extend entirely through pad P3'. Underneath the pad covering holes 20 is secured a relatively small pad or mat 22 made of highly absorbent or superabsorbent fibrous material. Mat 22 takes up all the liquid which drains through holes 20. The relatively small mat does not interfere with the overall gripping function of the rough, frictional, bottom surface 14. The drain hole or holes 20 may also be provided in pads P1 and P2 along with a liquid absorbing mat 22 when required at areas where liquids are likely to collect.

In FIG. 8 is shown another low friction pad P4' which has top lubricant layer 18c on foam layer 12c formed with a very smooth slippery surface 24, and a bottom rough, frictional surface 14. Mat 22 secured to surface 14 covers drain holes 20' to absorb liquids drained through holes 20'. Although layer 12c seems to be a single layer it is actually equivalent in functions to two bonded layers, as if both layers 12a and 16a, 12b and 16b were fused and bonded together to form a single integral but composite layer. Layer 12c has the slippery quality of the upper surfaces 16a' and 16" at its upper surface 24, and the bulk of spongy, foamy, cellular layer 12a or 12b below. The principal advantage of providing the one integral, composite layer 12c instead of two individual layers bonded together is economy in manufacture, which is very important in order to provide a pad which can be made and discarded after use at minimum cost to all concerned.

In FIG. 9 is shown a low friction foot sock 25 embodying a further modification of the invention. The sock may have an open or closed toe end 29. The sock has two generally cylindrical or tubular adjacent portions 27 and 28 to fit snugly around the foot and ankle respectively of a wearer of the sock. The sock has a multilayer low friction construction and can be made from any of the pads shown in FIGS. 1-8, except that drain holes 20, 20' and mats 22 may be omitted if not required. In the present instance sock 25 is shown as made of three layers, namely the bulky, foamy layer 12d on the outside, lubricant layer 18d on the inside, and intermediate layer 16d bonded to layer 12d and presenting a very smooth surface to layer 18d. The rough, frictional surface 14' faces outwardly. Layers 16d and 18d coact and cooperate to provide a shear reducing surface to the foot of the wearer. The sock 25 can be worn with or without a shoe, boot or slipper. If the sock is worn with a shoe or boot, the sock will serve as a very efficient antifriction device. The rough outer surface 14' will hold the sock in place in the shoe while the wearer's foot can slide frictionlessly in the sock. This type of sock can be used by bedridden persons, persons confined to wheelchairs, and others who are at risk of developing pressure and friction induced sores on on their feet. The socks can be used by runners for preventing or reducing chafing, abrasion, pressure, friction, shear and moisture induced sores. The sock can be used by athletes such as ball players, boxers, and by persons who must work or stand on their feet for extended periods of time while working or engaging in other activities.

The pads described above can be manufactured in the shapes of caps, gloves, socks, legging, armbands, etc. using any of the two, three or four layer structures illustrated in the drawings. The pads can be made in large or small sizes and in flat, tubular, concave, irregular, or special shapes to fit various parts of user's bodies, for low friction, shear force reducing applications.

The pads can be made in rectangular shape, in sizes large enough to cover the length and width of a bed, chaise longue, stretcher, gurney and the like, or they can be smaller to be inserted into briefs, diapers, underwear, pajamas, etc. to be worn by ambulatory or wheelchair confined persons. The pads can be made in circular, oval, and other regular and irregular shapes, and in various sizes. The pads can be made from other materials than those mentioned above. All of the pads described can be manufactured by mass production machinery at low cost from inexpensive materials, so the pads can be discarded after a single use or whenever soiled. The pads can be presterilized when manufactured. They can be individually packaged in throw away bags or envelopes. All of the pads can be made from biodegradable materials to decompose after they are discarded or they can be made from recyclable materials, which makes them ecologically acceptable.

While I have disclosed a plurality of embodiments of the invention, these have been by way of examples only. It will be understood that many modifications are possible without departing from the invention as defined in the following claims.

What is claimed is:

1. A multilayer low friction pad for reducing shear and friction forces on a person's body, and for preventing and treating sores on a person's body caused by shear forces, friction, pressure, chafing and moisture, comprising:
   a flexible first layer formed of a bulky foam material which is thick enough to serve as a shock absorber for an affected part of said person's body, and to prevent said pad from crumpling and wrinkling, and to facilitate handling the pad;
   a second layer bonded to one side of said first layer, said second layer being formed of thin, tough, flexible,, nonporous material to serve as a moisture barrier for preventing moisture from reaching said first layer;
   a third layer bonded at one side thereof to said second layer, said third layer being formed of a flexible material and having a very smooth and slippery other side; and
   a fourth layer composed of a slippery lubricant applied to and covering said other side of said third layer, said other side of said third layer being sufficient slippery to cooperate with said fourth layer to reduce shear forces thereon, and provide a working surface having a coefficient of friction of negligibly low magnitude.

2. A multilayer low friction pad as claimed in claim 1, wherein said first layer has an exposed other side formed with a sufficiently rough surface to grip frictionally a support to prevent displacement of said pad on said support while said person's body moves on said fourth layer.

3. A multilayer low friction pad as claimed in claim 1, wherein said first layer is formed of porous material for absorbing moisture collected on said third and fourth layers when said pad is rolled up to bring said first layer in contact with said fourth layer prior to discard of said pad after use.

4. A multilayer low friction pad for reducing shear and friction forces on a person's body, and for preventing and treating on a person's body caused by shear forces, friction, pressure, chafing and moisture, comprising:
   a flexible first layer formed of a bulky foam material which is thick enough to serve as a shock absorber for an affected part of said person's body, and to prevent said pad from crumpling and wrinkling, and to facilitate handling the pad;
   a second layer bonded at one side thereof to one side of said first layer, said second layer being formed of a flexible material having a very smooth and slippery other side; and
   a third layer composed of a slippery lubricant applied to and covering said other side of said second layer, said other side of said second layer being sufficiently slippery to cooperate with said third layer to reduce shear forces thereon and provide a working surface having a coefficient of friction of negligibly low magnitude.

5. A multilayer low friction pad as claimed in claim 4, wherein said first layer has an exposed other side formed with a sufficiently rough surface to grip frictionally a support to prevent displacement of said pad on said support while said person's body moves on said third layer.

6. A multilayer low friction pad as claimed in claim 4, wherein said first layer is composed of a nonporous material to serve as a moisture barrier for liquids collected on said second and third layers.

7. A multilayer low friction pad as claimed in claim 4, wherein said second layer is composed of nonporous material to serve as a moisture barrier for liquids collected on said second and third layers.

8. A multilayer low friction pad as claimed in claim 7, wherein said first layer is composed of porous material for absorbing liquids collected on said second and third layers when said pad is rolled up to bring said first layer into contact with said third layer prior to discard of said pad after use.

9. A multilayer low friction pad as claimed in claim 4, wherein said pad has at least one drain hole extending through all of said layers where liquid is likely to collect on said pad, said first layer having an exposed other side; and
   a highly absorbent mat secured to said other side of said first layer and covering said hole to absorb said liquid draining through said hole.

10. A multilayer low friction pad as claimed in claim 4, wherein said second layer is composed of porous material; and a nonporous fourth layer interposed between and bonded at opposite sides thereof to said first and second layers to serve as a moisture barrier for liquids collected on said second and third layers.

11. A multilayer low friction pad as claimed in claim 10, wherein said first layer has a free exposed side formed with a sufficiently rough surface to grip frictionally a support to prevent displacement of said pad on said support while said person's body moves on said third layer.

12. A multilayer low friction pad as claimed in claim 4, wherein said layers are shaped to nonflat configuration to conform with a nonflat part of a person's body.

13. A multilayer low friction pad as claimed in claim 12, wherein said first layer has a free exposed other side formed with a sufficiently rough surface to grip frictionally a support to prevent displacement of said pad on said support while said person's body moves on said support.

14. A multilayer low friction pad as claimed in claim 12, wherein said first layer is composed of nonporous material to serve as a moisture barrier for liquids collected on said second and third layers.

15. A multilayer low friction pad as claimed in claim 12, wherein said second layer is composed of nonporous material to serve as a moisture barrier for liquids collected on said second and third layers.

16. A multilayer low friction pad as claimed in claim 4, wherein said layers are shaped at least in part in a tubular configuration to extend around a part of a person's body.

17. A multilayer low friction pad as claimed in claim 4, wherein said layers shaped at least in part to define two tubular portions for extending around two parts of a person's body.

18. A multilayer low friction pad for reducing shear and friction forces on a person's body, and for preventing and treating sores on a person's body caused by shear forces, friction, pressure, chafing and moisture, comprising:

a flexible first layer formed of a bulky foam material which is thick enough to serve as a shock absorber for an affected part of said person's body, and to prevent said pad from crumpling and wrinkling, and to facilitate handling the pad;

a second layer composed of a slippery lubricant applied to and covering one side of said first layer, said one side of said first layer being sufficiently slippery to cooperate with said second layer to reduce shear forces thereon and provide a working surface having a coefficient of friction of negligibly low magnitude, said first layer having a free exposed other side formed with a sufficiently rough surface to grip frictionally a support to prevent displacement of said pad on said support while said person's body moves on said second layer;

first means for draining through said first and second layers liquid accumulating on said one side of said second layer; and second means at said other side of said first layer to collect and retain said liquid draining through said first and second layers.

19. A multilayer low friction pad as claimed in claim 18, wherein said first means comprises at least one drain hole extending through said first and second layers where said liquid is likely to collect on said layers; and wherein said second means comprises a highly absorbent mat secured to said other side of said first layer and covering said hole for absorbing any of said liquid draining through said hole.

* * * * *